United States Patent [19]
Sauter

[11] Patent Number: 6,149,815
[45] Date of Patent: Nov. 21, 2000

[54] PRECISE ELECTROKINETIC DELIVERY OF MINUTE VOLUMES OF LIQUID(S)

[76] Inventor: Andrew D. Sauter, 217 Garfield Dr., Henderson, Nev. 89014

[21] Appl. No.: 09/447,670

[22] Filed: Nov. 23, 1999

[51] Int. Cl.[7] .................................................. B01D 15/08
[52] U.S. Cl. .................... 210/635; 210/634; 210/656; 210/659; 210/767; 210/806; 210/314; 210/323.1; 204/450; 204/451; 204/600; 204/601; 422/100
[58] Field of Search .................................... 204/600, 601, 204/604, 450, 451; 422/99, 100; 210/635, 656, 659, 198.2, 634, 767, 806, 323.1, 314

[56] References Cited

U.S. PATENT DOCUMENTS

| | | | |
|---|---|---|---|
| 4,298,449 | 11/1981 | Ida | 204/600 |
| 5,174,882 | 12/1992 | DiSanto | 204/600 |
| 5,250,263 | 10/1993 | Manz | 422/99 |
| 5,425,858 | 6/1995 | Farmer | 204/600 |
| 5,603,351 | 2/1997 | Cherukuri | 204/269 |
| 5,605,662 | 2/1997 | Heller | 204/600 |
| 5,632,876 | 5/1997 | Zanzucchi | 204/600 |
| 5,645,702 | 7/1997 | Witt | 204/600 |
| 5,837,115 | 11/1998 | Austin | 204/600 |
| 5,856,100 | 1/1999 | Hayashizaki | 204/600 |
| 5,906,724 | 5/1999 | Sammons | 204/600 |
| 5,968,331 | 10/1999 | Kambara | 204/600 |
| 5,980,704 | 11/1999 | Cherukuri | 204/269 |
| 5,980,719 | 11/1999 | Cherukuri | 204/600 |
| 6,033,546 | 3/2000 | Ramsey | 204/600 |
| 6,042,709 | 3/2000 | Parce | 204/600 |
| 6,068,752 | 5/2000 | Dubrow | 204/600 |

*Primary Examiner*—Ernest G. Therkorn
*Attorney, Agent, or Firm*—Jacobson, Price, Holman & Stern, PLLC

[57] ABSTRACT

Femtoliter to milliliter volumes of one or a plurality of different liquids are accurately dispensed electrokinetically without any direct electrical contact with such liquid(s). This is accomplished with apparatus which creates an electric field over dispensing receptacles to discharge such liquid(s) into receiver reservoirs or scientific apparatus. Two electrically-conductive plates are insulated from each other so that a field polarizes the liquid and forces movement without faradaic processes or joule heating. One of the plates is charged, whereas the other is grounded. Liquid to be dispensed is placed between the two plates and is dispensed on applying the charge to the charged plate.

17 Claims, 2 Drawing Sheets

PRECISE ELECTROKINETIC DELIVERY OF MINUTE VOLUMES OF LIQUID(S)

BACKGROUND

Accurate and precise liquid movement to a destination is of interest in combinatorial chemistry, radioactive assays (due to ALARA concerns, i.e., exposure to radioactive solutions), in reducing environmental pollution and waste disposal costs, the accurate manufacturing of drug solutions and products, medical diagnostic testing, standards manufacture, in chemical analysis of explosives, agents and biologicals and in many other areas, including compound detection and purification of rare/expensive chemicals and drugs and other products by liquid chromatography. Low volume applications also exist in areas, such as filtration, compound isolation and extracting via solid phase extraction and related techniques, such as electroblotting and mass spectrometry, which are of high interest to many corporations, the defense community and research and development groups.

In these and related areas a wide range of mechanical dispensation devices are used, including, but not limited to, glass microliter syringes, manual multichannel (eight) pipettes, and derivatives thereof. None of these devices can accurately transport both nanoliter quantities and microliter quantities (from approximately 10 $\mu$l to 10−1 nl) with an error of a few percent, and hence they have a limited dynamic range. Moreover, none of these devices can simultaneously perform multiple functions in a highly precise manner (e.g., 24 or more channels), such as filtration, liquid chromatography, dispensation and other techniques that require fluid transport as a central operating mechanism at the same time using electrokinetic techniques that have no adverse electrochemistry, no joule heating, no moving parts and are arranged in a manner that allows non-experts to modify the function of the device easily for dispensation, liquid chromatography, filtration of other functions.

Because the physical movement of fluids is a central element of many processes, it is virtually impossible to adequately address all applications of pulseless nanoliter to microliter solution movement.

SUMMARY OF THE INVENTION

Apparatus electrokinetically transports and dispenses nanoliter or even femtoliter to microliter volumes of liquid (s) with an accuracy within a few percent. It comprises a switchable power supply device, two electrically-conductive plates, an upper plate and a lower plate, substantially parallel to and insulated from each other, the upper plate being chargeable or charged and the lower plate being grounded. A support for a receptacle is provided near, but below, the upper plate and directly above a receiving reservoir, which rests on the lower plate, supported by a nonconductor.

The apparatus is inexpensive to construct, and it has no moving parts. It can be employed to move or dispense one or more liquids with high accuracy and precision in a highly parallel manner (in up to and in excess of 100 channels). It can be operated in the femtoliter or picoliter to milliliter range with very high accuracy and precision, and be operated by non-sophisticated personnel using one source of power. It can simultaneously perform dispensation, liquid chromatography, filtration, extraction and electroblotting. It can concurrently perform any one or combination of such functions at the same or different rates. The apparatus can be easily and readily reconfigured by non-sophisticated personnel to perform dispensations, liquid chromatography (LC) or any other noted functions in a wide array of patterns.

Also, use of the apparatus employs intermolecular forces to transport liquid into or onto a target, or through chromatographic or other media to a desired position with high accuracy and precision when there is initially no continuous physical hardwired electrical contact between the liquid and the power supply device. This arrangement allows for precise and accurate movement of the liquid in and of itself or through media of interest with no need for high pressure fittings or tubing, a massive plumbing arrangement, sophisticated robotics or electronic devices. The apparatus can be augmented by various enhancements, for example robotic enhancements, to move dispensers.

An object of the invention is precise liquid transporting and dispensing in preferably nanoliter to microliter volumes and within an accuracy of ±5 percent. Another object is simultaneous plural dispensing of the same or different liquids in similar or varied nanoliter to microliter volumes. A further object is electrokinetic transporting and dispensing liquid in nanoliter to microliter volumes with no adverse electrochemistry, no electric contact with dispensing liquid, no pressure variation in liquid during flow, no joule heating and no moving parts. A still further object is simultaneously performing plural same or different functions, such as chromatography, filtration and spectrometry, on separate nanoliter to microliter samples of the same or different liquids. Another object is minimizing human exposure to carcinogenic, mutagenic or other harmful chemicals. A further object is separating and purifying components of a liquid composition by liquid chromatography without high pressure. A still further object is significantly reducing the amount of liquid needed for performing required tests or analyses. Another object is minimizing waste of valuable liquids or of those in short supply. A further object is providing apparatus to perform each of the foregoing. Still further objects are apparent from the following detailed description and examples.

DETAILS

Figure 1:
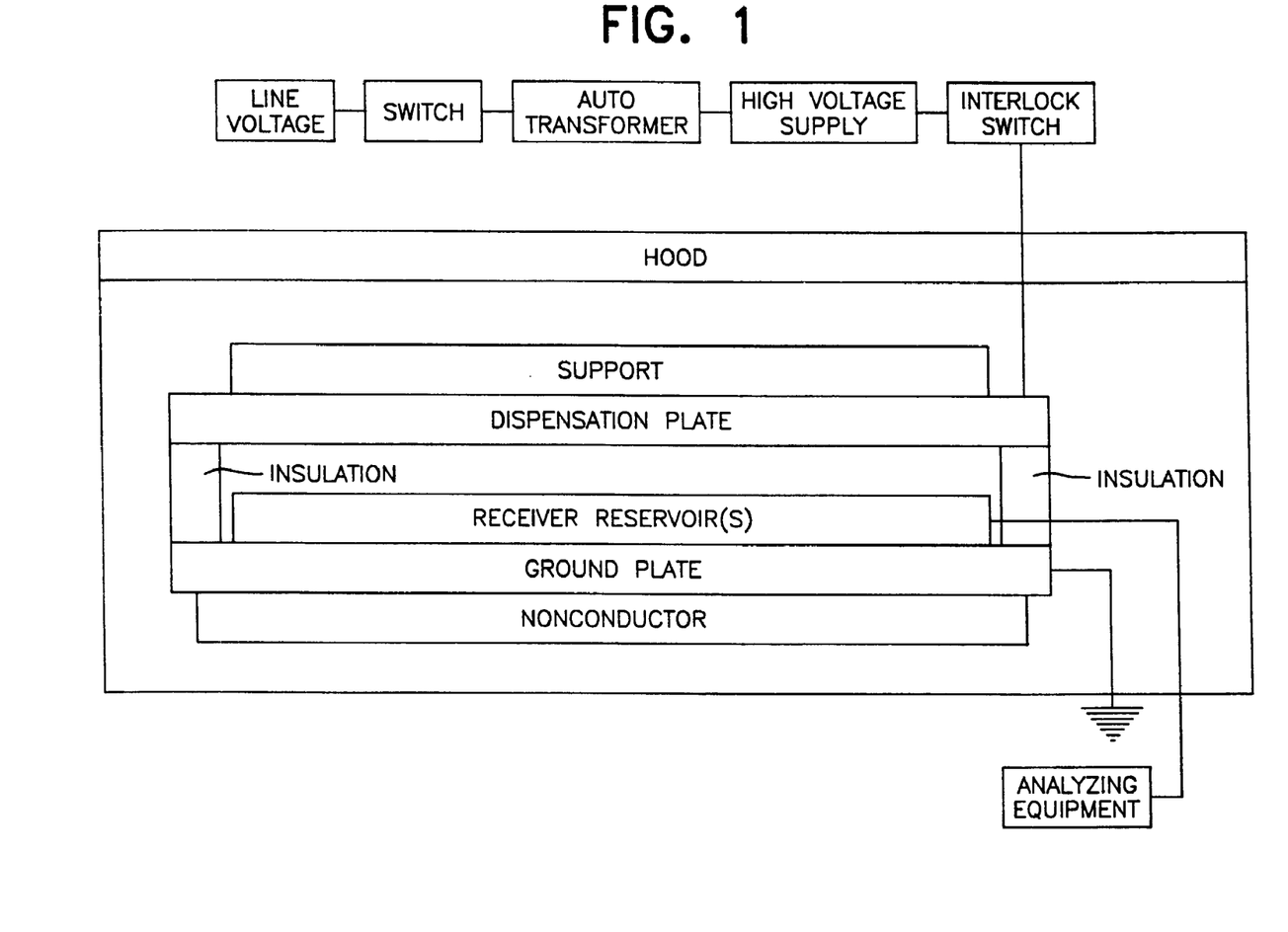
FIG. 1 is an overall representation of one apparatus set-up.

Femtoliter to milliliter volumes of the same or different liquids are electrokinetically dispensed or processed by relatively simple apparatus without any direct electrical contact to the liquid(s). With reference to FIG. 1, the apparatus comprises a dispensation plate electrically insulated from a ground plate which is deposed on a nonconductor, such as an insulated rubber mat. The dispensation plate is electrically conductive and is connected to line voltage, e.g., 120 or 240 volts.

Figure 3:
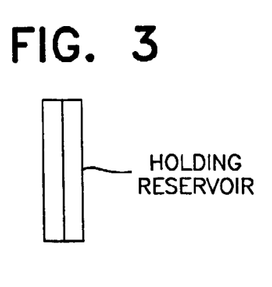
FIG. 3 is a representation of one embodiment of a holding reservoir.

In one embodiment a support is provided on the dispensation plate and contains, preferably, a plurality of receptacles, which extend (through holes in the dispensation plate) to positions between the dispensation plate and the ground plate. Each receptacle is designed to hold a liquid or a holding reservoir which, in turn, holds a liquid. The holding reservoir can be a capillary tube, as illustrated in FIG. 3, or other type of liquid container having an open lower liquid-discharge end. The cross-section of the holding reservoir is uniform or varied, and of circular, rectangular or other gaussian geometry. The representation of the receptacle in FIG. 4 is that of a pipette, but the specific shape of the receptacle is not so limited.

The support is, optionally, a PCR (polymer chain reaction) working and storage rack. Alternative supports which hold receptacles for liquids between the dispensation plate and the ground plate are readily substituted for the PCR racks. Each holding reservoir is optionally in direct communication with a more extensive liquid reservoir.

Figure 4:
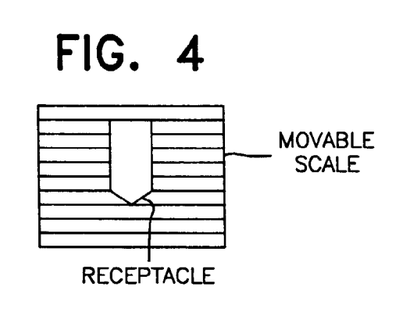
FIG. 4 is a representation of one embodiment of a receptacle and a corresponding movable scale.
Figure 5:
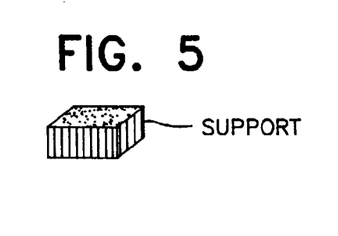
FIGS. 5 and 6 are representations of one embodiment of a support and of a receiver reservoir, respectively.

A movable scale is preferably placed adjacent to each receptacle to provide a measure of liquid dispensed from that receptacle, as shown in FIG. 4.

In one embodiment receiver reservoirs (supported by the ground plate) are positioned immediately below each receptacle so that liquid dispensed from each receptacle is actually dispensed directly into a particular receiver reservoir optionally, liquid from a plurality of receptacles can be dispensed into a single receiver reservoir. Thus, each receiver reservoir is positioned to receive dispensed liquid from one or more receptacles.

Figure 6:
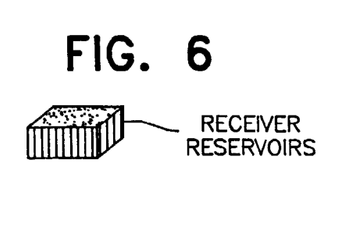

Receiver reservoirs can be in a form similar to that of the support (as shown in FIG. 6) or, alternatively, are in an individual cup or other suitable liquid-receiving form.

The entire operating portion of the apparatus is advantageously enclosed to avoid contamination of the liquid(s) being processed, and any such enclosure optionally comprises a hood to evacuate noxious or other fumes.

As shown in FIG. 1, line voltage is connected to a high voltage supply through a switch and autotransformer. The high voltage supply is connected to the dispensation plate optionally through an interlock switch.

Receiver reservoirs are optionally connected by suitable conduits to any of a variety of scientific apparatus, e.g., for conducting various analyses, such as mass spectrometry, infrared or ultraviolet spectroscopy, chromatography, etc.

Figure 2:
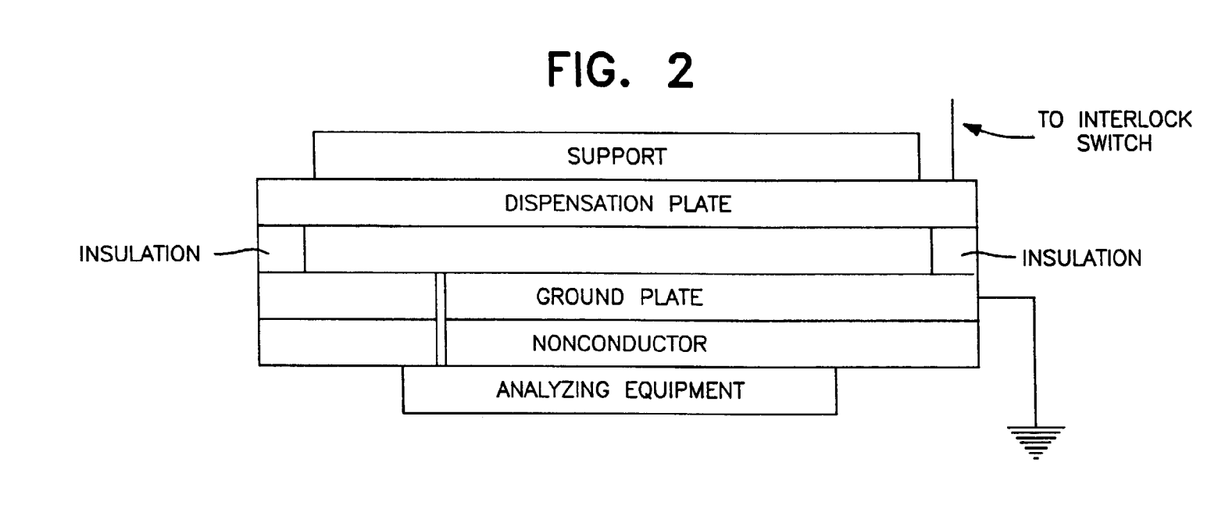
FIG. 2 is an optional alternative set-up for the operative portion of the apparatus.

In another embodiment of the invention, as represented by FIG. 2, the receiver reservoirs are replaced by a conduit which leads directly into scientific apparatus for testing and/or analysis. It is readily apparent that both embodiments can be provided in the same equipment, wherein some of the receptacles would dispense fluid directly into receiver reservoirs, whereas another receptacle would dispense fluid directly into a conduit leading into such scientific apparatus.

EXAMPLE 1

Parallel Precise Nanoliter Solution Movement

Cut three pieces of fused silica capillary (150 microns in diameter) tube (manufactured by Polymicro Technologies) coated with Teflon with a diamond tool to a length of 11 cm. Then insert these capillary tubes into clear plastic pipettes (Plastibrand, 20 microliter, cat. number 7025-76 manufactured by Brand), and cut off a length of 1.0 cm from the dispensing end of the pipette tips. Press a silicone plug into the upper opening of the wide end of the holding pipettes to restrain each inner dispensing capillary tube from moving. Ultrasonically degas 4.0 ml of dimethylsulfoxide in an ultrasonic cleaner (A Model 250 manufactured by E/MC, a Division of RAI Research). Introduce thus-degassed dimethylsulfoxide (liquid solvent) into each capillary tube by placing the capillary tubes, retained in the pipette tips, into the solvent, whereupon capillary action fills each capillary tube to the top. Place each pipette (with capillary tube) into a PCR (Polymer Chain Reaction working and storage rack) tube holding rack of 8×12 microtiter tube rack geometry (PGC Scientific, Cat. No. 48-486) where spacing between the capillary tubes is 9 mm, and each tube is linearly adjacent to another. Subsequently, place this assembly onto a dispensing plate. (The dispensing plate is made of aluminum, has a rectangular geometry of 10 cm×25 cm and 1.5 mm thick, and in which 96 holes have been drilled in standard, 9 mm, 8×12 microtiter plate geometry.) Place the dispensing aluminum plate directly over another (receiving) plate of identical geometry, but which does not contain holes. Place a standard plastic microtiter plate (to which aluminum foil is carefully pressed into three receiving "cups") on top of the receiving plate. Attach the aluminum foil so that the foil touches the receiving plate. Arrange the dispensing plate so that it rests in a position over the receiving plate and is separated from the receiving plate by insulators of approximately 5.0 cm in height. Set the complete apparatus so that it rests on an insulating rubber mat. Connect the dispensing plate to a 30 kV, 20 watt high-voltage power supply, and connect the receiving plate to ground potential. Connect the power supply to a variable autotransformer (Staco Energy Products Co., Type 3PN1010) which has a switch that can be employed to turn the power supply on and off and a dial which can be employed to vary the positive potential applied to the dispensing plate from a 120 volt line input.

Place a scale (printed on paper and affixed to a plastic retainer) directly behind the capillary tubes. The scale is based on the fact that the radius of the capillary in each tube is a constant 75 microns, and hence the distance that the liquid moves is directly correlated with the volume dispensed. Focus a video camera Panasonic PV-1958 tight (6×) in on the tubes so that the tubes are seen directly in front of the scale. Connect the camera to the video input of an RCA 2000 color monitor, and set the video equipment at approximately a 45 degree angle so that the liquid and the meniscus can be seen directly on the monitor and recorded on video tape.

To effect solution movement, apply a positive 15 kV to the dispensing plate to move the solution down in all three tubes simultaneously. Turn off the power after 176 nl are dispensed or the meniscus moves approximately 1.0 cm in each of the tubes. No further movement occurs; that is, the solvent stops dispensing. Inspect the cups visually to verify that liquid is received by each cup, and the volume of a bead of solution is observed to be visually identical in each cup. The distance traveled by each meniscus is virtually the same, and no difference is discerned visually even on the monitor. Repeat this experiment five times to obtain virtually identical results. The volume thus moved is approximately 177 nl±8.8 nl.

EXAMPLE 2

Discrete and Continuous Parallel Precise Nanoliter Solution Movement

Repeat Example 1 in an identical configuration and in an identical manner, but cycle the switch between the on an off positions. View the result and record the solution moving in a stepwise fashion, stopping rapidly when the power is off and immediately moving upon power-up conditions. Conduct 20 approximately equal cycles over a 1.0 cm or 176 nl total volume movement to confirm discrete parallel solution movement of approximately 9.0 nl. Review the video on the monitor and use a ruler to measure each discrete movement to establish an estimated error of 9.0 nl±1.5 nl.

After discrete parallel dispensation, turn on the power at 15 kV for continuous dispensation. This set of experiments moves the solvent in a discrete fashion. Recording by video and using a ruler (scale) to measure solution movement in discrete and continuous fashion, the discrete dispensation is estimated at 9.5 nl±1.8 nl, and the continuous dispensation over 1.0 cm (estimated) is 179±4.6 nl.

EXAMPLE 3

Single 176 Nanoliter Dispensation into a Standard Nonconducting Microtiter Plate With apparatus of Example 1 (except where discussed below) fill one 12 cm length of 150 micron diameter fused silica capillary tube (coated with Teflon) via capillary action to the top with a solution made from 10 ml of 50% ethanol in water to which 4 drops of each of red (FD&C Red 40), green (FD&C Yellow 5 and FD&C Blue 1), blue (FD&C Blue 1) and yellow (FD&C Yellow 5) dye (all dyes distributed by Schillings as assorted Food colors and Egg Dye by McCormick & Co., Inc.) are added. The resulting black solution is visible to the naked eye in the capillary tube. Place a standard microtiter plate between the dispensing plate and the ground plate. Place the capillary tube in the holding rack so that the tip of the capillary tube does not touch the microtiter plate, and is approximately 0.5 cm from the base of the receiving cup in the microtiter plate, which has a total thickness of 1.25 cm. Place the several plates so that the total separation between the positive (dispensing) plate and the ground plate is 5.0 cm.

Charge the dispensing plate to a positive +15 kV, to move the dye solution into the nonconducting microtiter plate (Nunc brand MicroWell U96 polypropylene, 0.5 ml, 96 well standard configuration). Conduct a series of five dispensations to observe that it takes from 46 to 50 seconds for the solution to move 1.0 cm or 176 nl as viewed by the naked eye and using a manual switch to initiate and stop flow. In each case examine the microtiter plate to find one small bead of dark solution in the bottom, typically very near the center, of the microtiter plate well.

Hence accurate single dispensation into a nonconducting standard microtiter plate is observed with the apparatus.

EXAMPLE 4

Multiple Single Dispensation of 1473 nl±75 nl into a Nonconducting Microtiter Plate with Recovery of Solution Following the procedure of Example 3, except that the diameter of the fused silica column is 250 microns, prepare the dispensing solution from 20 ml of a stock solution of 50% ethanol and water with 5 drops of red dye (FD&C Red 40) added. Fill the tubes to the top and place them so that they can be visually observed against the scale. Charge the dispensing plate to a positive +15 kV to initiate dye flow until the solution moves an estimated 3.0 cm, dispensing a nominal 1473 nl with an estimated read error of 5.0% or 75 nl. After each of five individual dispensations into the nonconducting microtiter plate, observe the target well to find a bead of solution near the center of the well.

In this set of experiments, with a relatively large volume, remove the capillary tube from the holding rack and employ capillary action in an attempt to recover the solution dispensed to the microtiter plate. The five tries should result in recovery of from 89 to 94 percent of the original solution dispensed into the nonconducting microliter plate, and visual evidence reveals that some solution remains in each microtiter plate well. Also there is no visual evidence that splattering or other loss of solution occurs. This is believed to be due to an effect similar to field focusing inherent in the geometry of such arrangements for conductors and potentially for nonconductors.

EXAMPLE 5

Single Dispense and Subsequent Deposition onto Nitrocellulose Strips

Using apparatus of Example 1, remove a known quantity of a liquid solution from a tube and then deposit it on a nitrocellulose strip (Millipore SPHF nitrocellulose). Cut one piece of 180µ id fused silica tubing with a diamond tool to 11 cm lengths. Burn off polyimide with a propane torch from approximately half of each tube to allow visual inspection of the tubes' contents. Then cut the tubes to a total length of 7.5 cm. Fill each tube by capillary action with a 50% solvent solution of ethanol and water to which 4 drops of red food coloring dye (FD&C Red 40) is added to 10 ml of the solvent. Change the scale of Example 1 to reflect the different volume/distance relationship. Also in these examples visually observe and correlate the solution and it's relationship to the scale without the aid of a video camera and monitor.

Conduct a set of experiments with continuous flow and with discrete flow. For example, in the first experiment dispense the solution and visually correlate it with a distance scale so that 2.0 cm or 308 nl move. Remove the tube from its holding device, and blow the solution carefully onto a nitrocellulose strip to produce a red spot observable under a microscope (American Optical Corp. 50). Measure the spot's radii by reference to a scale and cross hatchings in the scope. Observe symmetrical spots with an average diameter of 0.398 mm±6.3%.

Hence the device can be employed to remove known quantities of liquid for subsequent transfer to another medium, such as a nitrocellulose strip.

EXAMPLE 6

Single Dispensation of Nanoliter Quantities of Heparinized Human Blood onto Two Nonconductors Insert human blood into a 7 ml Vacutainer Brand Sterile vial (id code 367676, BF855, Dec. 1999 expiration date) containing solid sodium heparin. Subsequently, expose the blood to a capillary tube of fused silica of 250 micron diameter and 7.5 cm total height from which the polyimide exterior has been burned off with a torch. Affix the capillary tube to the pipette tip and retain it in the PCR rack as in Example 1. Place a standard plastic 8×12, 9 mm separation microtiter plate between the dispensing plate and the ground plate.

Once the blood containing capillary tube is placed into retainers on the dispensing plate, initiate flow by the application of a positive 15 kV to the dispensing plate. Stop the dispensation by manually switching off the applied potential when the blood, which was easily visible, in the capillary tube has traveled 1.0 cm, producing a bead of approximately 490±24.5 nl in the microtiter plate well. Repeat the experiment three times to obtain transfer times for the blood of from 9.8 to 10.3 seconds for the volume traveled.

Repeat essentially the same experiment three times but, in each case, place the blood on microscope slides thus producing three regular, symmetrical spots (roughly 2.2 mm in diameter) of blood on the slides within a dispensation time for each nominal 491 nl of blood of from 9.8 to 10.5 seconds.

EXAMPLE 7

Single Dispensations of 19.6 nl±1.0 nl Solution onto a Nonconducting Microtiter Plate Repeat Example 1 using one capillary tube of 50 microns in diameter and a red-dye solution (i.e., 20 ml of 50% ethanol in water with 4 drops of red dye (FD & C Red 40) added to it). Place a standard 8×12 microtiter plate between the pipette tip and the ground plate, as in Example 4. Execute a single dispensation, taking the dispensing plate to a positive 15 kV, and visually stop dispensing the solution after it travels 1.0 cm as referenced to the scale or the volume equivalent of 19.6 nl±approximately 1.0 nl. Observe extremely small beads of solvent in the microtiter plate well's central axis.

EXAMPLE 8

Nanoliter Production of Droplets onto Nonconductors Using an Exit Modified Tip

Cut 250 micron fused silica capillary tubes to a length of 7.0 cm and modify the tip of each to produce an approximate ball at the opening of 0.5 mm in diameter, which partially restricts the flow of liquid out of the tubes. Place a single dispenser so modified into the dispenser plate as in Example 1. Use liquid identical to that in Example 5.

Initiate power to a positive 15 kV to produce spherical droplets at a relatively constant rate for the first 10 seconds on a nitrocellulose strip (Millipore, SPHF nitrocellulose) as the strip is moved to offer a fresh surface place according to the rate of droplet production.

EXAMPLE 9

Single Nanoliter Solution Movement of Nonpolar Hexane into a Nonconducting Microtiter Plate Repeat Example 1 by dispensing spectroscopic grade hexane (nonpolar solvent) as the liquid from a 150 micron capillary column, 10 cm high, into one well of a standard nonconducting microtiter plate.

For this example, draw the hexane into the tube by a partial application of a small vacuum. Apply a positive +15 kV to move the nonpolar solvent (in from 21 to 23 seconds) 2.0 cm±approximately 5% (i.e., 350 nl±5.0%).

This is an important example, as nonpolar solvents cannot be moved by other electrokinetic techniques.

EXAMPLE 10

Highly Parallel LC Column Packing and Highly Parallel no Pressure Liquid Chromatography Manually plug twenty-four transparent pipette tips (Plastibrand, 20 microliter, outlet id a nominal 0.35 mm, cat. number 7025-76) with approximately 1 to 2 mg of glass wool using a plunger. To these pipette tips, add a slurry of Hypersil C 18 Spherical, 3 micron liquid chromatography (LC) solid phase (manufactured by Hypersil) in a 50% mixture of ethanol and water. Place 2.0 cm of PVC tube on the top of each tip, and place a 50% ethanol/water solvent and a slurry of the solid phase in each PVC tube. Take the power supply to +15 kV to express the solvent simultaneously from all 24 pipettes onto the receiving plate, thus packing the columns substantially uniformly. After approximately ten minutes, turn off the voltage.

Remove excess solid phase so that the solid phase is exactly at the top of each pipette. Make a black colored solution by placing 5 drops of each of blue (FD & C Blue 1), red (FD & C Red 40), green (FD & C yellow 5 and FD & C Blue 1) and yellow (FD & C yellow 5) food dyes (Schillings) into 20 ml of a 50% ethanol and water solution. Carefully add 5.0 μl of the solution to the top of each pipette, using a microliter syringe. After approximately 5 minutes, place the PVC attachment again on the top of the tips, and place 300 μl of the 50% ethanol and water solvent rapidly on the top to serve as a solvent reservoir. [Note: arrange the array of tips in a standard 96 microtiter plate arrangement, but with a 3×8 geometric arrangement of the pipette tips. That is, separate the 24 tips in a rectangular (3×8) array with their centers separated by 9 mm.]

Take the dispensing plate to a positive 15 kV to move the solvent into 24 metallic cups (spent 9 mm ammunition casing shells manufactured by Novinco of China) placed on the receiving plate directly under the tips, which are approximately 0.5 cm from the plate itself. Over a period of approximately 35 minutes, the 24 pipette tips containing the LC packing phase express liquid into the receiving cups. As the experiment continues during this time, observe bands of color moving down the column and into the vials. First a yellow band moves through the column; then, sequentially, an orange, red, blue, purple, and light purple bands elute from the column. During the experiment, the color development or movement is visually obvious in each column. Collect and view the solution in the vials after each band. As the pipette tips are conical, the rate of flow increases down the column, and hence the colored bands accelerate away from each other, down the column. Most of the 24 columns develop color in a manner that demonstrates very similar retention behavior and hence flow, as required by the van Deemter equation.

Once a colored band is observed to elute from the column, stop the experiment by turning off the positive potential. Visually observe the solutions in the receiving cups. Note solutions of yellow, orange, red, blue, violet and light purple in the course of a thirty-five minute experiment, verifying that the mixed dyes are separated. At the end of the experiment note that the liquid chromatography phase is its original white color. Transport the dyes to cups, having effected highly parallel 24 channel separation and collection of the organic compounds. The cups for every color band for every color contain a bead at the center of the cup. No color is observed outside the receiving vessel.

EXAMPLE 11

Eight Channel Parallel Dispensation of 982 nl±49.1 nl

Cut eight pieces of 250μ id fused silica capillary tubes with a diamond tool to 11 cm in length. Burn off polyimide over approximately half of each tube to allow visual inspection of each tube's contents. Place the tubes in a dispensing plate in a linear array where the spacing between the tubes is 9 mm. For the liquid use a solvent comprising a 50% mixture of ethanol and water, with four drops of red (FD & C Red 40) food coloring dye added to each 10 ml. The apparatus is that of Example 1.

Place the capillary tubes into plastic holders and fill them by capillary action by moving an array with the eight capillary tubes all at once. Move the discharging plate with the holding reservoirs or tubes back to the insulators above the receiving plate, make a scale of paper denoting seven lines one cm apart (vertically), and place same on a plastic plate mounted on the dispensing plate so that the distance of liquid movement is visually correlated with column length. Apply a positive 15 kV to the intact device containing the eight dispensers to obtain flow of the reagent into small metal containers (spent 9 mm ammunition casing shells manufactured by Novinco of China) similar to the wells of standard microtiter plates. Stop and start flow at will, without any leakage, by cycling the power supply between high and low values. Move the liquids in all eight dispensers 2.0 cm in approximately 10 seconds with no more difference in the height moved than approximately 1 mm or 1 part in twenty, or 5%.

EXAMPLE 12

Simultaneous Single Channel Dispensation, Liquid Chromatography and Filtration

Cut a 150 micron capillary tube into several sections, and place one section (tube 1) in a pipette tip as described in Example 1. Next, construct an LC column (tube 2) as described in Example 10. Fashion a filtration device (tube 3) using a pipette tip to which a 5 micron Teflon filter has been fixed to the tip and held in place by using a 1/16 inch grommet manufactured by Buchanan.

Fill tube 1 by capillary action with a 50% solution of ethanol and water and place it on the dispensation plate with 8×12 holes arranged in standard 9 mm geometry. Then add 20 μl of black mixed dye solution with a microliter syringe, as in Example 10, to the tip of tube 2, and place this device on the same dispensation plate laterally adjacent from tube 1. After 5 minutes, place a 2.0 cm long piece of Tygon tubing (0.25 inch id) on the top of the tip of tube 2 and fill it with a 50% solution of ethanol and water. Then fill tube 3 with a 50% solution of ethanol and water, and place it on the dispensation plate adjacent to tube 2. Place a standard 8×12 microtiter plate such that any three wells on the plate line up vertically with tubes 1, 2 and 3, and put a scale with 1.0 cm vertical grids on the scale in back of the tubes.

With all tubes on the dispensation plate, apply a positive 15 kV to the dispensation plate, keeping the ground plate at ground potential. Observe the level of solution in tube one against the scale and, when it has moved three centimeters (approximately 25 seconds), or 528 nl, turn off the potential and remove tube 1. Then turn on the power to a positive 15 kV and reinitiate the flow in tubes 2 and 3. After 10.0 minutes, turn off the power on the dispensation plate. Remove tube 3, and observe the well beneath to which approximately 10.0 μl of solvent has been transported as it was filtered by the Teflon filter into the well on the microtiter plate underneath tube 3. Once again turn on the power to 15 kV on the dispensation plate to effect liquid chromatography in tube 2, as the color bands (yellow, orange, red, blue, purple and dark purple) are sequentially deposited into the microtiter plate from the original black solution. As such, the device performs simultaneous dispensation, filtration and liquid chromatography.

EXAMPLE 13

Serial Nano-filtration, Nano-Extraction, Liquid Chromatography and Nano Dispensation With apparatus of Example 1, attach a 5 micron Teflon filter with O-rings to a piece of 1/4 inch PVC (2.0 cm in height) tubing filled with 50% ethanol in water solvent. Attach this filtration reservoir to one well removed from an Ansys solid phase extraction plate with filter (Spec. Plus. 96-Well.C2, Diagnostics, Inc., Cat. No. 596-01) containing 15 mg of C2 extraction media. Couple this device to a transparent pipette tip (Plastibrand, 20 microliter, cat. number 7025-76) which is manually plugged with approximately 1 to 2 mg of glass wool using a plunger. Add a slurry of Hypersil C18 liquid chromatography solid phase (3 micron) in a 50% mixture of ethanol and water to these pipette tips and pack the solid phase. Place a standard microtiter plate between the dispensing and the receiving plates. Hydrologically connect the filter, extraction device, and LC column serially together. Place the resulting device in the PCR rack as per Example 1.

Place 50 μl of a black aqueous solution (made up from 4 drops of each of red, blue, green and yellow food coloring—Schilling) into the filter reservoir, and charge the discharge plate to a positive +15 kV, to commence flow from the filter to the extraction device, filtering the black solution and depositing it onto medium in the extraction well.

After approximately 15 minutes, turn off the power and remove the filter. Add a 50% solution of ethanol and water to the filter. Power up the system again to a positive 15 kV to move the dyes into the liquid chromatography column in roughly ten minutes to effect liquid chromatography as the dyes separate over the length the column and are deposited into one well of a standard nonconducting 96 well extraction plate. Turn off the power upon the elution of a given color band; remove the single colored solution with a microliter syringe, and place it in a vial. The entire procedure takes approximately 50 minutes, realizing serial filtration, extraction, liquid chromatography and dispensation.

EXAMPLE 14

Charged, Power Down, Simultaneous Dispensation of 175±35 nl and 700 nl±25 nl into a Nonconducting Microtiter Plate Containing a Liquid With apparatus of Example 1, using fused silica capillary tubes of 150 micron in diameter and liquid comprising 50% ethanol in water, impress a positive potential of 15 kV on the dispensing plate for 15 seconds and then turn off the power to stop liquid flow. Bring a microtiter plate containing 200 μl of water into physical contact with liquid in the discharge end of each of the capillary tubes simultaneously to observe power-down simultaneous dispensation of the ethanol/water liquid into the water in the microtiter plate. Such dispensation is approximately 327 nl±9.0 nl in each tube.

Repeat the foregoing with the solvent, dimethylsulfoxide, as the liquid, placing it into the capillary tubes to form a column 10 cm in height. Impress a positive potential of 15 kV for approximately 5 seconds to discharge approximately 1.0 cm of solvent from each capillary tube. Then, with a microtiter plate containing 200 μl of water, bring the surface of the water in the is microtiter plate into physical contact with the solvent at the discharge end of each of the three capillary tubes simultaneously to effect dispensation of the solvent into the receiving water in an amount of approximately 700 nl±35 nl from each tube.

COMMERCIAL APPLICATION

In the discovery of new drugs using combinatorial chemistry techniques literally thousands of drug candidates are made by chemists and are subsequently tested by a variety of techniques to see whether they have desired bioactivity. This is almost always conducted in a solution phase, or solutions are required to be measured and placed in various containers, such as microtiter plates. In combinatorial chemistry, accurate and precise solution dispensation and removal are required to be conducted on thousands of small volumes of solutions per day to conduct such studies. Also, combinatorial chemistry requires that microliter and, ideally, nanoliter quantities be handled to, for example, transport to other reservoirs, synthesize candidate drugs, introduce into a scientific instrument for analysis and for other purposes. It is likewise key that such reagents are not oxidized or reduced by electrochemical phenomena; and it is often important that they not be heated to avoid unwanted chemical reactions. Hence, a device that can accurately dispense and otherwise transport nanoliter and microliter quantities of liquids has direct application to the discovery of new drugs via the technique of combinatorial chemistry. Also, there is a need for a device capable of moving solutions either singly or in parallel, the efficiency of which directly assists the improvement in efficiency of new drugs. Devices that employ pneumatic, peristaltic or other pumps cannot address the dynamic range of such a device (in fact they cannot dispense nanoliters with high accuracy and precision), and they require complex pumping and robotic systems to execute such functions if they attempt true parallel operation at all.

The utilization of GREINER Plates in combinatorial chemistry and other related applications employs many different well types, but many are of small physical size, in the order of 12 $\mu$l. Known devices cannot be employed for transporting nanoliters to microliters of liquids with high precision and accuracy to nonconducting and conducting media of diverse forms and in many geometric arrangements; available devices do not have an extensive dynamic range and cannot concurrently be employed to allow dispensation into large plates of 384 and 96 well plate geometry by a simple dispensing plate modification.

DNA can be analyzed by many techniques, but in typical electrophoretic analysis of this biopolymer, manual DNA microliter solution placement is often performed into the gel. Prior devices do not dispense both microliter and nanoliter quantities of solutions using charge injection, which would render older less accurate manual placement techniques obsolete. Apparatus is desired for increasing the precision and accuracy of DNA analysis, and extremely precise and accurate sample deposition is required for that purpose.

Also in biochemical and genetic research the isolation and the subsequent analysis of proteins, oligonucleotides, various biopolymers and other chemical constituents of human cells and of various other biochemical in physiological fluids or tissues of a chemical entity can be extremely small and, due to the cost of isolation of the material, extremely valuable. A device, a) which can help improve the utilization of such rare "chemicals" in various types of experiments by producing solutions of known concentration from microliter to nanoliter quantities and thus less wasted material, and b) which can enable more experiments and analyses for a given amount of extremely rare and costly biochemical and other compounds of interest to genetic and other research, is needed.

Environmental regulation (i.e., The 1976 Resource and Conservation Act) requires that chemicals and other fluids be handled and disposed of in a costly manner (i.e., in regulated landfills). The costs of such regulated disposal can be 10 to 100 times that of non-regulated landfill disposal. In chemical analyses and other applications of the subject apparatus, waste production can be reduced by a factor of one hundred to one thousand, as much less mass of regulated compounds is needed to be employed, for example, for an accurate standard solution (or other reagents) for calibration of scientific instruments, medical diagnostic testing equipment or other applications. Hence, the ability of a device to dispense small quantities of liquids accurately can dramatically reduce waste disposal costs to laboratories, manufactures of solutions and products and others that currently use microliter dispensation devices. Also, since the apparatus can be employed to reduce the total amount of reagents needed for a given task, less chemicals and other reagents or agents can be employed, reducing production costs of standard solutions, chemical products and other liquid products.

Human exposure to chemicals and other reagents is related to the concentration of the chemical constituents, and the federal government has derived equations that attempt to quantify the risk associated with exposure to a given chemical or reagent. Since the subject apparatus can be employed to use smaller quantities of material for a given end, less exposure to harmful, carcinogenic, mutagenic or other harmful materials results when this device is employed. The federal government recognizes that risk of chemical exposure is related to the concentration of a chemical in a given locale. By using this apparatus, a much lower volume of a chemical of a given concentration can be used to perform a test or for other purposes, and hence risk associated with exposure can be reduced. This implies directly that using smaller quantities of a given substance has beneficial health and exposure effects. The instantly presented apparatus can reduce the amount of material or chemicals needed to effect a given process by at least two to three orders of magnitude compared to those devices that dispense or otherwise move chemicals in the microliter quantity range for research and development, in medical testing, in product or drug manufacturing and in other applications. Hence, since the apparatus can move nanoliter quantities of fluids with high accuracy and precision, reduced human exposure to chemicals results in a health benefit.

Also, as the manual glass microliter syringe was invented many years ago to reduce exposure of humans to radiation, the instant apparatus, which can move nanoliters with high precision and accuracy, can directly reduce the exposure of workers and others to radiation AS REQUIRED BY THE NATIONAL USDOE ALARA DOCTRINE (radiochemical exposure must be As Low As Reasonably Achievable) by a factor of 100 to 1000 for equally radioactive solutions contained in older devices that can manage only microliter dispensation.

Similarly, since the device can move quantities of biological fluids with high accuracy and precision in the nanoliter volume range, it can reduce human exposure to pathogens, HIV and other diseases or disease-causing agents by simply reducing the amount of material needed or employed for a diagnostic test or other related purpose in clinical laboratories, in chemical laboratories and elsewhere.

Liquid chromatography is a powerful technique that can be employed to purify chemicals, drugs and other materials. It is also used to separate chemicals in mixtures, such as drugs of abuse in physiological fluids, pesticides in water, anions and cations in water and many other important applications which are of defense, military, counter terrorism, environmental and other interest. Currently liquid chromatography devices cost roughly $20,000 to $70,000, and they perform largely one analysis at a time. This analysis time can range from a few minutes to thirty minutes or greater for one sample. The ability of the subject apparatus to perform multiple liquid chromatographic experiments simultaneously (24 at a time and higher) has major economic and technical application of import to industry and government.

The utility of the device is particularly important with the government's widely publicized counter terrorism efforts and related investigations. For example, in the TWA 800 investigation chemical analysis for explosives was conducted by the government and its agents using, among other techniques, liquid chromatography. These analyses could have been conducted at east twenty-four times faster if the subject apparatus had been employed. Such efficiency not only could aid the investigation in terms of efficiency but, because many more samples could have been analyzed per unit time, greater spatial and temporal resolution could have been realized, directly effecting the total information picture available to the authorities.

Similarly, the application of analysis techniques to military, defense or counter terrorism purposes, such as detection of land mines, detection of radiochemicals in battle field environments, nerve agents and degradation products thereof and other toxins and chemicals, could be made much more efficient than current equipment, which does one analysis at a time. Faster response, which has a parallel advantage, can increase response time, as it decreases cost in significant applications of liquid chromatography and related techniques of import to defense, military, counter terrorism and other fields of interest to the federal government and its agents.

Another major advantage of employing the subject apparatus for liquid chromatography is that the device executes separation or purification of a sample or a chemical without HIGH PRESSURE. Commercially available LC units employ high pressure (from roughly 500 to 6000 psi) to effect liquid chromatography. Typically, pneumatic pumps push a mobile phase through an analytical column that performs the separation. The subject apparatus pulls the solution through an analytical column using van der Waals forces. Hence no costly high-pressure fittings or other devices (e.g., the analytical column) are required to withstand high pressure. Thus, tubing and other components (e.g., fittings) can be made of inexpensive materials, reducing total instrument and analysis costs significantly. Moreover, commercially available liquid chromatographic devices (i.e., high pressure liquid chromatography) produce a pulsed flow which complicates detection by increasing detector noise. The subject apparatus produces a smooth flow and therefore can facilitate and improve detection limits compared to pulse-flow systems.

Kebarle has published, as have others, on the electrochemistry that occurs during electrospray ionization mass spectrometry. This phenomenon can cause chemicals undergoing ESI/MS and ESI/MS/MS analysis to be oxidized or reduced. This property of all ESI sources results in decreased sensitivity and in qualitative analysis difficulties as one compound can become more than one via E, EC and ECE mechanisms (i.e., electrochemical complications). The subject apparatus can produce ESI spectra that are free of electrochemical phenomenon and related complications which hinder chemical analysis by mass spectrometry (e.g., cystiene oxidation), assisting applications in proteomics, and many other areas that employ ESI as an introduction technique to mass spectrometers.

In many areas of research, and in the production of medical diagnostic test strips it is often advantageous to deposit small quantities of a fluid to a NONCONDUCTING or conducting medium, such as nitrocellulose strips, microscope slides or other devices. This apparatus can deposit very small (10 nl) or much larger (10 µl) quantities of liquids onto such media or devices, expanding the dynamic range of such tests. Hence the sensitivity of the deposition for whatever purpose can be increased or decreased depending on the needs of the test (e.g., reading a microscope slide, manufacturing diagnostic test strips, and so forth) with simple configurational changes of the device.

The parallel advantage of the subject apparatus is extremely important. For example, in computer science, it is recognized that concurrent task execution dramatically improves the speed of computers and hence parallel processors are employed to do multiple things at the same time. Similarly, using this apparatus to perform one function or many functions can be realized, concurrently reducing task execution time and thereby increasing efficiency of any process whether it is drug solution manufacturing, solution dispensation for chemical or medical analysis or for other purposes.

Scientific instruments or instruments or devices that make products (e.g., drug solutions) and so forth can be expensive. Typically the cost increases with the number of times that it can perform a single function. Also cost can increase for the number of functions that a device can execute. Such devices are typically "hardwired" to effect one function, or multiple functions in a serial manner. The device described in this filing has a physical footprint that can be easily and economically reconfigured to perform one function at a time, one function many times, multiple functions, one at a time, or multiple functions concurrently or sequentially. Other devices cannot be so configured or reconfigured singly or in parallel by non-experts.

For example, a microliter syringe or a manual pipette cannot execute dispensation and liquid chromatography or filtration at the same time in the microliter or nanoliter volume regime. The subject device cannot only perform multiple functions, it can do so concurrently and it can be easily reconfigured to produce an instrument that can do one function, one at a time, one function many times, multiple functions one at a time or multiple functions many times. The nature of the device is unique in this manner, as it can be easily converted into a range of devices that can perform multiple functions using reservoirs that are largely inexpensive. Hence, since the device can be easily reconfigured by non-experts for a variety of functions, the device can significantly reduce the cost of scientific instrumentation and other instrumentation that produce products (e.g., drug solutions) and that have fluid movement in common.

The invention and its advantages are readily understood and appreciated from the foregoing description. Various changes may be made in the apparatus, in individual components thereof or in the method without departing from the spirit and scope of the invention or sacrificing its material advantages. The process and apparatus hereinbefore described are merely illustrative of preferred embodiments of the invention.

What is claimed is:

1. Apparatus which is a) useful for accurately transporting or dispensing one liquid or for accurately transporting or dispensing a plurality of the same or different liquids, in similar or different microliter to picoliter volume ranges, and, optionally, is b) useful for performing one or more other operations concurrently or sequentially on the same or different liquids and which comprises: one or more non-conducting receptacles, an electrically conductive dispensation plate, one or more targets, a grounded plate, insulation, a nonconductor of electricity, a high voltage supply, and an on/off switch;

each receptacle having an outlet secured in a support and being in a position between the dispensation plate and a corresponding target;

each target being conducting or non-conducting and being between the dispensation plate and the grounded plate;

the insulation being between the dispensation plate and the grounded plate and insulating each of these plates from the other;

the grounded plate being supported by the nonconductor; and     the high-voltage supply being connected, through the switch, to the dispensation plate.

2. Apparatus of claim 1 wherein each target is a receiver reservoir supported by the grounded plate.

3. Apparatus of claim 1 wherein the high voltage supply is provided with an arc-protection circuit.

4. Apparatus of claim 1 wherein at least one receptacle is packed with chromatographic packing material.

5. Apparatus of claim 1 wherein at least one receptacle comprises a filter or sequential filters.

6. Apparatus of claim 1 wherein at least one receptacle comprises solid phase extraction medium.

7. Apparatus of claim 1 in combination with one or more holding reservoirs, each of which being supported in one of the receptacles and comprising a tube having an internal channel, the cross section of which is uniform or varied and of circular, rectangular or other gaussian geometry.

8. Apparatus of claim 1 in combination with one or more holding reservoirs, each of which being supported in one of the receptacles and comprising a capillary tube having an inner diameter which is the same as or different from that of any other holding reservoir.

9. Apparatus of claim 8 which further comprises a movable scale adjacent to at least one of the receptacles.

10. Apparatus of claim 8 which comprises a plurality of holding reservoirs.

11. Apparatus of claim 10 wherein at least one of the holding reservoirs has an inner diameter or an effective inner diameter which is different from that of another holding reservoir.

12. Apparatus of claim 8 wherein each holding reservoir is a non-conducting capillary tube of one fixed inner diameter in the range of from one micron to a few millimeters in diameter.

13. Apparatus of claim 8 wherein each holding reservoir is a non-conducting capillary tube, each of which, independently, has an inner diameter in the range of from one micron to a few millimeters.

14. A method of separating components of a liquid composition by passing the composition through the chromatographic packing material in apparatus of claim 4 by creating a sufficient voltage difference over the composition.

15. A method of filtering a liquid composition by passing the composition through the filter(s) in apparatus of claim 5 by creating a sufficient voltage difference over the composition.

16. A method of extracting a liquid composition by passing the composition through the extraction medium in apparatus of claim 6 by creating a sufficient voltage difference over the composition.

17. A pulseless method which comprises accurately and electrokinetically transporting or dispensing one liquid or a plurality of the same or different liquids in similar or different microliter to picoliter volume ranges and, optionally, performing one or more other operations concurrently or sequentially on the same or different liquids with apparatus of claim 1.

\* \* \* \* \*